(12) United States Patent
Cole

(10) Patent No.: US 10,471,741 B2
(45) Date of Patent: Nov. 12, 2019

(54) METHOD OF INKJET PRINTING ONTO ALIGNERS

(71) Applicant: Align Technology, Inc., San Jose, CA (US)

(72) Inventor: Michael Christopher Cole, Longmont, CO (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 16/439,450

(22) Filed: Jun. 12, 2019

(65) Prior Publication Data
US 2019/0291474 A1     Sep. 26, 2019

Related U.S. Application Data

(63) Continuation of application No. 15/945,224, filed on Apr. 4, 2018, now Pat. No. 10,336,102.
(Continued)

(51) Int. Cl.
*B41M 5/00* (2006.01)
*B41J 3/407* (2006.01)
(Continued)

(52) U.S. Cl.
CPC ............... *B41J 11/002* (2013.01); *A61C 7/08* (2013.01); *B41J 3/4073* (2013.01);
(Continued)

(58) Field of Classification Search
CPC .......... C23C 14/22; C23C 14/28; B41J 3/407; B41J 3/4073; B41J 11/002; B41M 5/0017; B41M 5/0047
See application file for complete search history.

(56) References Cited

U.S. PATENT DOCUMENTS 6,371,610 B1   4/2002   Nakamura et al.
6,599,559 B1   7/2003   McGee et al.
(Continued)

FOREIGN PATENT DOCUMENTS

WO   WO 2018/187434   * 10/2018   .............. B41M 5/00
WO   WO-2018187434 A1   10/2018

OTHER PUBLICATIONS

International search report with written opinion dated Jun. 27, 2018 for PCT/US2018/026031.
(Continued)

*Primary Examiner* — Huan H Tran
(74) *Attorney, Agent, or Firm* — Wilson Sonsini Goodrich & Rosati

(57) ABSTRACT

Provided herein are methods of obtaining good photocured-ink adhesion to low surface energy materials. The methods have greatly improved adhesion of photocured ink on low surface energy materials, including those that are subjected to high humidity or wet environments. The methods take into account the glass transition temperature ($T_g$) of the materials and the onset for the glass transition temperature, including ink applied to an exposed surface of the material at an elevated temperature that is close to the $T_g$ of the material. The ink is allowed to sit briefly or soak, such as for more than 1 second, before the ink is cured. The ink may be photocured. Furthermore, the methods do not require solvents or surface treatment, including plasma or corona treatments, to obtain good ink adhesion.

24 Claims, 4 Drawing Sheets

Related U.S. Application Data

(60) Provisional application No. 62/481,491, filed on Apr. 4, 2017.

(51) Int. Cl.
  *B41J 11/00* (2006.01)
  *C09D 11/322* (2014.01)
  *C09D 11/101* (2014.01)
  *A61C 7/08* (2006.01)
  *B41M 7/00* (2006.01)

(52) U.S. Cl.
  CPC ........ *B41M 5/0011* (2013.01); *B41M 5/0017* (2013.01); *B41M 5/0047* (2013.01); *B41M 5/0064* (2013.01); *C09D 11/101* (2013.01); *C09D 11/322* (2013.01); *B41J 3/407* (2013.01); *B41M 7/009* (2013.01); *B41M 7/0081* (2013.01)

(56) References Cited

U.S. PATENT DOCUMENTS

| | | | |
|---|---|---|---|
| 10,336,102 B2* | 7/2019 | Cole | B41M 5/0017 |
| 2007/0247502 A1 | 10/2007 | Grant et al. | |
| 2008/0299327 A1 | 12/2008 | Salleo et al. | |
| 2008/0300824 A1* | 12/2008 | Culp | A61C 7/08 702/166 |
| 2011/0104405 A1 | 5/2011 | Saitou et al. | |
| 2017/0007362 A1 | 1/2017 | Chen et al. | |
| 2017/0008333 A1 | 1/2017 | Mason et al. | |
| 2017/0275482 A1 | 9/2017 | Kogure et al. | |
| 2019/0009576 A1 | 1/2019 | Cole et al. | |

OTHER PUBLICATIONS

Modern Plastics Handbook. Harper (McGraw-Hill 2000). Chapters 1.1-1.2: 1-88.
U.S. Appl. No. 62/189,259, filed Jul. 7, 2015.
U.S. Appl. No. 62/189,263, filed Jul. 7, 2015.
U.S. Appl. No. 62/189,271, filed Jul. 7, 2015.
U.S. Appl. No. 62/189,282, filed Jul. 7, 2015.
U.S. Appl. No. 62/189,291, filed Jul. 7, 2015.
U.S. Appl. No. 62/189,301, filed Jul. 7, 2015.
U.S. Appl. No. 62/189,303, filed Jul. 7, 2015.
U.S. Appl. No. 62/189,312, filed Jul. 7, 2015.
U.S. Appl. No. 62/189,317, filed Jul. 7, 2015.
U.S. Appl. No. 62/189,318, filed Jul. 7, 2015.

* cited by examiner

METHOD OF INKJET PRINTING ONTO ALIGNERS

CROSS-REFERENCE TO RELATED APPLICATIONS

This application is a continuation of U.S. patent application Ser. No. 15/945,224, filed Apr. 4, 2018, now U.S. Pat. No. 10,336,102, issued on Jul. 2, 2019, which claims the benefit of U.S. Provisional Application No. 62/481,491, filed Apr. 4, 2017, which are hereby incorporated by reference in their entireties.

BACKGROUND

Orthodontic procedures typically involve repositioning a patient's teeth to a desired arrangement in order to correct malocclusions and/or improve aesthetics. To achieve these objectives, orthodontic appliances such as braces, retainers, shell aligners, and the like can be applied to the patient's teeth by an orthodontic practitioner and/or a patient. The appliance is configured to exert force on one or more teeth in order to effect desired tooth movements. The application of force can be periodically adjusted (e.g., by altering the appliance or using different types of appliances) in order to incrementally reposition the teeth to a desired arrangement.

It may be desirable to provide designs and/or written information on the surface of the aligner. Many aligner surfaces, however, present challenges with respect to reliable printing. In particular, ink adhesion can be challenging in view of the low surface energy material that forms many aligners, including plastics and polymers. In addition, the oral environment in which many aligner are used may be wet, may have high humidity, high temperature, and/or saliva containing various enzymes and other components designed to break-down materials. An oral environment may also cause mechanical rubbing against an aligner therein, making reliable and safe ink printing on the aligner surface challenging, particularly for an extended duration of time. Additionally, labels affixed to the surface of an aligner, particularly one in an oral environment, may present challenges. Although etching is useful in some contexts, such as those described in U.S. Pat. Pub. No. 2017/000833 filed Jul. 5, 2016 titled "Dental Appliance Having Ornamental Design," etching may not be useful in some contexts.

BRIEF SUMMARY

Various embodiments disclosed herein provide robust, reliable and readily implemented ink printing to the surface of a low surface energy material, such as low energy surface material used to form aligners and/or low energy surface materials used in an oral and/or other wet and/or high humidity environment. Provided herein are systems and methods of printing ink to a low surface energy material. The methods may include applying an ink to an exposed surface of the material at an elevated temperature. In some embodiments, the elevated temperature ($T_e$) is greater than or equal to onset temperature associated with the low surface energy material's glass transition temperature. In some embodiments, $T_e$ is less than or equal to the glass transition temperature ($T_g$) of the low surface energy material, The elevated temperature may include ranges of $T_g-70°$ C.$<T_e<T_g+70°$ C., and any subranges thereof. In this manner, ink applied to the surface, including a printable ink applied by inkjet printing, may be left for a soak time at the elevated temperature, in some embodiments, facilitating penetration below the surface. The ink may then be cured, to verify likelihood of durable adhesion with the low surface energy material, including likelihood of durable adhesion in a high humidity and/or wet environment where conventionally applied ink without the elevated temperature and soak time steps would quickly release from the material.

The systems and methods provided herein may result in a number of functional benefits. For example, the methods may ensure a robust and reliable ink printing onto surfaces and for applications that are normally incompatible with ink printing. For example, the ink printing may be compatible with relatively harsh environments and materials that are typically incompatible with the ink, including surfaces characterized as low energy, hydrophobic, or non-polar. Typically, such surfaces do not reliably receive printable ink, with the applied ink characterized as readily damaged or removed, including in liquid environments, high-humidity environments or mechanically abrasive environments.

In some embodiments, the systems and methods are compatible with inkjet printing. Inkjet printing processes are particularly useful because a wide range of properties may be controlled, including any spatial distribution pattern of ink to form logos, designs and/or alphanumeric text, and the like. Color is also readily controlled and applied, including multi-colored printing. Inkjet printing is further compatible with contoured surfaces, whereas other printing techniques, such as pad printing, are more challenging. Inkjet printing may also ensure the printed patterns are individually and readily customizable.

The systems and methods are also compatible with a wide range of ink-curing techniques, including electromagnetic curing of a photocurable ink. The methods may also be functionally beneficial by reducing processing time and treatment. For example, no surface treatment is required, thereby reducing overall process time.

The systems and methods provided herein may be characterized as providing high adhesion, including ink remaining adhered, including after a 24-hour water soak test. For ink patterns that remain visible without substantial ink release after a 24-hour water soak test, the ink may be characterized as being durably adhered to the low surface energy material. "Durably adhered," as used herein, may be quantitatively and/or qualitatively defined. For example, durably adhered may be characterized by at least 90% of the printed ink remaining adhered to the exposed surface after immersion in water for an immersion time in water of at least 24 hours. The water may be at or near human body temperature or near oral cavity temperature. In some embodiments, the temperature of the water may be substantially near human body temperature, e.g., within one or more of 20%, 10%, or 5% of human body temperature. In other embodiments, the temperature of the water may be much greater than body temperature such as when a printed device is placed into a dishwasher for a cleaning cycle. In this latter embodiment, the device may experience an elevated temperature that is greater than the material's $T_g$ but the exposure time will tend to be short (less than 24 hours, and more typically less than 30 minutes). Ideally, the cleaning temperature is less than the $T_g$ of the material. Soaps and other cleaning agents may be present during such cleaning.

Any of the systems and methods provided herein may be compatible with inkjet printing of the ink to the surface of a low surface energy material. Many conventional processes for ink adhesion to low surface energy substrates may rely on the use of solvents. Such solvent use, however, may provide complications due to nozzle clogging issues as well as emitted volatile organic compounds (VOCs). Additionally, the solvents often absorb into the substrate which then becomes a potential health hazard or irritant for medical devices, including dental aligners. Sometimes, surface treating with plasma or corona is used to increase the surface energy by creating polar groups on the surface of the polymer; this may present, however, an added step in the process and may add cost. In many conventional processes, the increased surface energy may increase adhesion of ink to a substrate but may prevent the ink from balling up when applied to the surface since the inks are typically polar and the untreated surface is nonpolar. When the ink spreads out onto a treated surface, the resolution of the printing process is potentially decreased. The methods provided herein can advantageously avoid such problems in the art. Accordingly, any of the methods provided herein may be for printing of ink onto low surface energy materials without surface pretreatment. However, in some embodiments, the methods described herein are compatible with any one or more surface treatments.

Provided herein are systems and methods of printing ink to a low surface energy material. The method may comprise: heating a low surface energy material to an elevated temperature that is less than a glass transition temperature (Tg) of the low surface energy material; applying a printable ink to an exposed surface of the heated low surface energy material; soaking the applied printable ink and the low surface energy material for a soak time; and curing the printable ink applied to the exposed surface after the soak time. In this manner, the cured printable ink may be further characterized as durably adhered to the low surface energy material, including sufficiently adhered to maintain adhesiveness with the surface in a high humidity and/or wet environment.

The elevated temperature may be less than the glass transition temperature, $T_g$, but within 70° C. of the $T_g$, including within 20° C. of the $T_g$. The minimum temperature to which the low surface energy material should be heated before ink application may be described as corresponding or equal to the $T_g$ onset temperature. In various embodiments, $T_g$ is a temperature at which a material transitions from a hard glassy state material to a viscous or rubbery state, and is also described as the "leathery region" of the material. $T_g$ characterizes the range of temperatures over which glass transition occurs, particularly as $T_g$, for many materials, is not related to a simple phase transition. Accordingly, any of the methods provided herein may be characterized as having an elevated temperature corresponding generally to the $T_g$ onset temperature, including a minimum elevated temperature before ink application that is equal to or greater than the $T_g$ onset temperature.

In some embodiments, the systems and methods disclosed herein are compatible with various manners of heating, including heating by radiative or convective heating and/or any other manner of heating. For example, heating the low surface energy material may include exposing the the low surface energy material to infrared light having wavelengths that are matched to an absorbance spectrum of the low surface energy material, to substantially confine heating to the exposed surface, thereby avoiding a bulk material property change to the low surface energy material.

The heating step may be substantially confined to a printing area of the exposed surface or to a geometric shape having a border area in which the applied ink is confined. For example, a rectangle heated area may be generated, with ink provided within the boundary of the rectangle heated area, but not necessarily applied to the entire heated area. The amount of coverage of printable ink may be expressed in terms of the surface area of the printed ink ($A_{ink}$) to the heated surface area of the material ($A_{heated}$), such as $0.1 < A_{ink}/A_{heated} < 1$. A value of 1 or close to 1 may be achieved, for example, by heating the ink so that the surface heated corresponds directly to ink applied to the surface. For embodiments where the surface itself is heated, the upper limit of the ratio may be less than 1, such as $0.1 < A_{ink}/A_{heated} < 0.95$.

The substantially confined heating may be by any one or more of: directed infra-red heating and/or directed hot air jet; to the printing area.

The method may further comprise sensing temperature in or adjacent to the printing area, and printing the printable fluid for a sensed temperature that corresponds to a desired elevated temperature. Adjacent, in some embodiments, may be a location having a temperature reading that reliably reflects the temperature within the printing area.

The heating step may comprise heating of the printable ink, so that heating of the low surface energy material is, at least in part, by physical contact of the heated printable ink to a printing area on the exposed surface.

The heating may be by one or more of: infrared radiation; microwave radiation; contact heating with a heating element; ultrasonic radiation; radiofrequency heating; heated air; and heated liquid. In some embodiments, a source of infrared radiation, microwave radiation, contact heating, ultrasonic radiation, radiofrequency heating, heated air, and/or heated liquid is provided to supply the heating.

The elevated temperature may also be expressed in absolute terms, particularly for materials of interest having glass transition temperatures greater than 70° C. For example, the elevated temperature may be between 70° C. and 130° C.

In some embodiments, applying a printable ink to an exposed surface of the heated low surface energy material may comprise printing a visual design to the exposed surface. In such embodiments, "durably adhered," as used herein, may be characterized by a visual design remaining substantially unaltered after a significant immersion time in a relevant liquid at a temperature of a relevant cavity, such as an immersion time in water of at least twenty four (24) hours, including at a water temperature corresponding to temperature in an oral cavity. In some embodiments, a printed visual design may have a surface area, and the printed visual design being "substantially unaltered" corresponds to at least 90% of the surface area remaining optically visible after an immersion time in water of at least 24 hours, such as at a temperature of an oral cavity.

In some embodiments, ink applied to the exposed substrate may be described as having an applied optical intensity, and the printed design being "substantially unaltered" may correspond to a post-immersion optical intensity after an immersion time in water of at least 24 hours that is within at least 90% of the applied optical intensity.

In various embodiments, the method may have a soak time that is less than or equal to 30 seconds, or less than or equal to 20 seconds, and generally greater than 0.8 seconds, or 1 second.

The method may further comprise selecting an ideal soak time from the elevated temperature value and the $T_g$ and providing the soak time that is substantially equal to the ideal soak time.

The method may have an ideal soak time having a lower value for relatively higher elevated temperatures.

In some embodiments, the ideal soak time may be between 0.8 seconds and 1.2 seconds for an elevated temperature that is within 2° C. of the $T_g$, and, as the elevated temperature decreases further from $T_g$, a corresponding increase in ideal soak time.

The soak time may be selected to achieve a desired maximum penetration depth of the applied ink into the low surface energy material. For example, the maximum penetration depth may be at least 10 μm, at least 5 μm, or at least 1 μm from the low surface energy material exposed surface.

In some embodiments, applying a printable ink to an exposed surface of the heated low surface energy material may comprise ink-jet printing of the printable ink from an ink jet printer. In some embodiments, the ink jet printer is provided.

In various embodiments, the printable ink may be heated before or during the ink-jet printing. As noted herein, in various embodiments, the printable ink may be heated to a temperature that is greater than or equal to 60° C., or greater than or equal to 100° C.

The method may be compatible without surface treatment, so that any of the methods may relate to an exposed surface that is not pretreated prior to the applying step. However, in some embodiments, the method is compatible with surface treatment, as desired. Accordingly and alternatively, the method may further comprise pretreating the exposed surface before the applying step.

Examples of pretreating may include one or more of: washing the exposed surface; chemically treating the exposed surface; mechanically treating the exposed surface; radiatively treating the exposed surface; plasma treatment; or corona treatment.

The low surface energy material may comprise a plastic. Examples of plastics include, but are not limited to, a plastic or mixtures of plastics selected from the group consisting of: a polyolefin, a polyester, a polyacrylate, polymethacrylates, polystyrenes, polypropylenes, polyethylenes, polyethylene terephthalates, poly lactic acid, polyurethanes, epoxide polymers, polyethers, poly(vinyl chlorides), polysiloxanes, polycarbonates, polyamides, poly acrylonitriles, polybutadienes, poly(cycloolefins), and copolymers.

The low surface energy material may comprise a thermoset or thermoplastic.

The low surface energy material may comprise a polymer, including a polymer used to form an aligner, such as an aligner used for orthodontic applications.

The printable ink may comprise a pigmented resin, including a pigmented resin that is curable with application of heat, light, water or air.

In some embodiments, curing the printable ink may comprise exposing the printed ink to electromagnetic radiation, including electromagnetic radiation having a wavelength in the visible spectrum or ultraviolet spectrum.

The printable ink may comprise a dual cure system having a cationic component and a free radical component.

The printable ink may have a low molecular weight component that diffuses into the low surface energy material to a depth from the exposed surface.

The low surface energy material may be a polymer and the printable ink diffuses into the polymer and at least partially plasticizes the polymer.

In some embodiments, curing the printable ink may occur after the printable ink penetrates to a depth below the exposed surface, so that after the curing step the printable ink is at least partially embedded in the low surface energy material.

In some implementations, "high adhesion" and/or "durable adhesion," as used herein, may be characterized by polar binding and/or covalent binding of the printable ink to the low surface energy material.

Any of the methods provided herein may be substantially solvent free.

Any of the methods may further comprise coating the printed printable ink with an overcoat layer.

A representative method for use for an application related to dental aligners may include the following elements: A material is provided. If dirty, and if deemed necessary, the material is cleaned (one or more cleaning systems are used such as alcohol, water, soap, $CO_2$ jets, ultrasonic, etc.). The material is cut into smaller pieces that can fit a single aligner. The material then is thermoformed into the aligner. The temperature of the aligner is monitored and when the temperature is in the range (70° C. to 130° C.), the inkjet pattern is printed onto an exposed surface of the aligner. The ink is allowed to sit on the hot materials from 250 ms to 30 s and then exposed to a light source that cures the ink. The aligner is then allowed to cool. Once cooled, laser marking or other functions may be performed on the aligner. The aligner can then be cut, cleaned, and packaged.

As desired, any of the methods may use one or more of: a Corona pretreatment then inkjet printing; Plasma treatment then inkjet printing; Isopropanol wash and corona treatment then printing; Isopropanol only then printing; heat sample to 90° C. then apply ink, wait 10 s, then cure.

The methods provided herein may be useful for a range of applications beyond aligners. Examples of such applications include those having low surface energy materials that may be used in water and where surface indicia is desired to be long lasting. Examples include: bath toys, medical devices, pipes, including underground pipes, etc. The inkjet printing provided herein is particularly useful where the surface indicia is required to be customizable.

The methods may be compatible with other printing methods beyond inkjet. For example, pad printing can obtain the same wet adhesion capabilities as the described inkjet method. In some embodiments, inkjet printing may be preferable over pad printing for substrates having surface contours or irregularities (where pad printing may provide an inability to reliably print any shape on demand). For such applications, a stamp may be needed for the pad print method and so reliable contact difficult over the entire stamp for irregularly contoured surfaces.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION

Figure 1A:
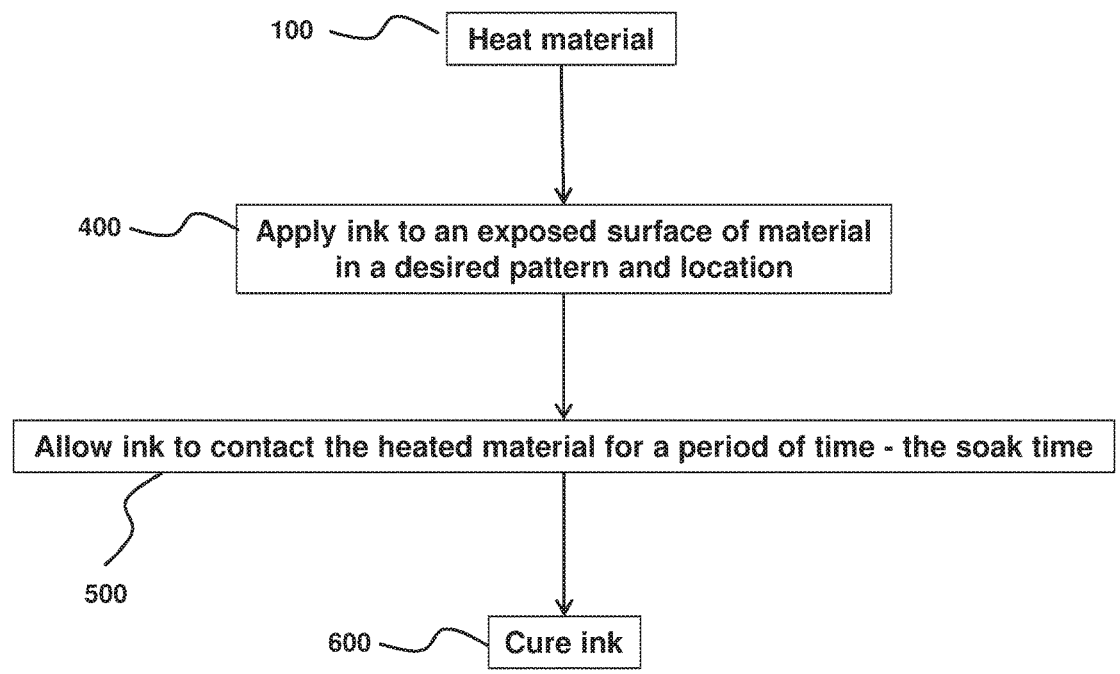
FIGS. 1A and 1B are flow-chart summaries of examples of methods of ink-jet printing to a surface of a material.

In general, the terms and phrases used herein may have their art-recognized meaning, which can be found by reference to standard texts, journal references and contexts known to those skilled in the art. The following definitions are provided to clarify their specific use in the context of the invention.

"Low surface energy material," as used herein, may refer to a material that is generally characterized as hydrophobic or non-polar, and so does not receive printable ink well, and provides challenges for achieving good ink adhesion to a surface. Various examples of low surface energy materials are provided herein.

"Exposed surface," as used herein may refer to a surface of the low surface energy material that is capable of being exposed to printable ink, including printable ink applied by ink-jet printing. Accordingly, any surface that faces and has a line of sight with a nozzle of the inkjet printer may be characterized as an exposed surface.

"Elevated temperature" of a low surface energy material, as used herein, may refer to a temperature of the low surface energy material, where at least a portion of the surface has an average temperature that is greater than an otherwise resting temperature (for example room temperature), and is greater than or equal to the glass transition temperature onset temperature. Optionally, the elevated temperature may be less than the glass transition temperature ($T_g$) and greater than or equal to the onset temperature associated with the $T_g$ of the low surface energy material. Optionally, the elevated temperature may be greater than the glass transition temperature ($T_g$) of the low surface energy material. Functionally, the elevated temperature may facilitate ink penetration, and so can be accomplished by any number of techniques. As discussed, the material itself may be heated. Alternatively, or in addition, the ink may be heated, so that upon impact with the material, the ink acts to heat the material. The elevated temperature may be confined to an exposed surface of the material. In some embodiments, the elevated temperature may be confined to the to-be-printed region, and regions immediately adjacent thereto.

Depending on the application of interest, elevated temperature may be greater than or less than $T_g$. For example, improved adhesion and shorter soak times may be achieved for elevated temperatures above $T_g$. In certain applications, however, it may be desired to not go above $T_g$, so as to minimize risk of an unwanted shape change or deformation to the aligner, or to minimize risk of a crystallinity change. In other applications, such as an application where risk of unwanted aligner shape is minimized, such as for an aligner that is in contact with a mold, ink application may occur immediately following a thermoforming step and so may be occur at a temperature greater than $T_g$.

The methods and systems provided herein are also compatible for materials having a $T_g$ and $T_g$ onset temperature above room temperatures, including for a $T_g$ and $T_g$ onset temperature 20° C. or more above standard room temperatures, and including for with materials with $T_g$ and $T_g$ onset 40° C. or more above standard room temperature. As used herein, "standard room temperature" may refer to a temperature of about 20° C.

"Glass transition temperature" ($T_g$), as used herein, may refer to the range of temperatures over which glass transition occurs. $T_g$, in particular, characterizes the transition from a glassy state to a rubbery state, and is characterized as having a temperature range or a "leathery region." See, e.g., Modern Plastics Handbook. Harper (McGraw-Hill 2000) 1.2 and Figure 1.1. Accordingly, "onset of the glass transition temperature" refers to a temperature at which the transition begins. Techniques are available to measure glass transition onset temperature. Techniques include, for example, Differential Scanning calorimetry (DSC), Thermo Mechanical Analysis (TMA), and Dynamic Mechanical Analysis (DMA). See, e.g., *Polymer Handbook*, CRC Materials Science and Engineering Handbook, Third Edition (Edited by James F. Shackelford and William Alexander, CRC Press 2000).

"Durably adhered," as used herein, may refer to an adherence property of a material (e.g., an ink). Durably adhered, as used herein, may refer to a material remaining adhered to a surface, even under high humidity or wet conditions, and being able to withstand abrasive, rubbing, and/or other mechanical forces. Whether a material is durably adhered to another can be assessed by any number of tests, including abrasiveness tests and/or liquid immersion tests (e.g., water immersion tests). In some embodiments, a process that results in the printed ink remaining adhered at a desired level, such as greater than 75%, greater than 90%, greater than 95%, greater than 99%, or 100%, after a 24 hour water immersion test, including for water at a temperature corresponding to the oral cavity, may be characterized as durably adhered, including for a standard adhesive test such as by a tape test.

"High humidity" or "wet environment," as used herein may refer to environments having a substantial liquid aspect. For example, the oral cavity of a living animal, including a human, may be considered herein to be a high humidity and a wet environment. Immersion, total or partial, in a liquid may also be considered a wet environment.

Unless explicitly defined otherwise, "substantial," as used herein, may refer to a value that is within at least 20%, within at least 10%, or within at least 5% of a desired value, or that is equal to a value.

"Soak time," as used herein, may refer to the time elapsed between ink application/contact with the substrate and the process of curing. A precise soak time may depend on process conditions and material variables, including temperature, ink composition, material composition and shape, for example. Similarly, an application of interest in which inked material will be used may influence soak time. For example, applications requiring stronger adhesion may have a longer soak time than applications where a lesser adhesive force is suitable.

"Operably coupled," as used herein, may refer to a configuration between two or more components such that the functionality of each component is maintained. Operably coupled may include configurations in which components are directly connected to each other as well as configurations where components are indirectly connected to one.

"Fluid communication," as used herein, may refer to a configuration between two or more components such that fluid may be controllably transferred from one component to the second component, such as a nozzle of an ink-jet printer that applies ink to an exposed surface of a material.

"Polymer," as used herein, may refer to a molecule composed of repeating structural units connected by covalent chemical bonds often characterized by a substantial number of repeating units (e.g., equal to or greater than 3 repeating units, optionally, in some embodiments equal to or greater than 10 repeating units, in some embodiments greater or equal to 30 repeating units) and a high molecular weight (e.g. greater than or equal to 10,000 Da, in some embodiments greater than or equal to 50,000 Da or greater than or equal to 100,000 Da). Polymers are commonly the polymerization product of one or more monomer precursors. The term polymer includes homopolymers, or polymers consisting essentially of a single repeating monomer subunit. The term polymer also includes copolymers which are formed when two or more different types of monomers are linked in the same polymer. Useful polymers include organic polymers or inorganic polymers that may be in amorphous, semi-amorphous, crystalline or semi-crystalline states.

"Polymer network," as used herein, may refer to a polymer composition comprising a plurality of polymer chains wherein a large portion (e.g., ≥80%) and optionally all the polymer chains are interconnected, for example via covalent crosslinking, to form a single polymer composition. In an embodiment, there is provided a radiopaque polymer in the form of a crosslinked network in which at least some of the crosslinks of the network structure are formed by covalent bonds.

"Monomer," as used herein, may refer to a reagent which can undergo polymerization under one or more specified conditions. A monomer reagent may comprise at least one monomer molecule, where a monomer molecule is a molecule which can undergo polymerization, thereby contributing constitutional units to the structure of a macromolecule or oligomer. In an embodiment, a monomer reagent may be represented by an average or dominant chemical structure and comprise monomer molecules having that chemical structure but may also contain components with other chemical structures. For example, a monomer reagent may comprise impurities having chemical structures other than the average or dominant structure of the reagent. An oligomer or oligomeric reagent is also a reagent which can undergo polymerization under appropriate conditions. An oligomeric reagent comprises an oligomer molecule, the oligomer molecule comprising a small plurality of units derived from molecules of lower relative molecular mass. In an embodiment, certain hyperbranched crosslinking reagents suitable for use with the invention may be regarded as oligomeric reagents.

Photoinitiators are disclosed herein. In some embodiments, photoinitiators may be useful for various purposes, including for curing of ink, including those that can be activated with light and initiate polymerization of the polymerizable components of the formulation. In embodiments, the photoinitiator is a radical photoinitiator and/or a cationic initiator. In some embodiments, the photoinitiator is a Type I photoinitiator which undergoes a unimolecular bond cleavage to generate free radicals. In an additional embodiment the photoinitiator is a Type II photoinitiator which undergoes a bimolecular reaction to generate free radicals. Common Type I photoinitiators include, but are not limited to benzoin ethers, benzil ketals, α-dialkoxy-acetophenones, α-hydroxy-alkyl phenones and acyl-phosphine oxides. Common Type II photoinitiators include benzophenones/amines and thioxanthones/amines. Cationic initiators include aryldiazonium, diaryliodonium, and triarylsulfonium salts.

In some embodiments, photopolymerization occurs when suitable formulations are exposed to light of sufficient power and of a wavelength capable of initiating polymerization. The wavelengths and power of light useful to initiate polymerization depends on the initiator used. In various embodiments, light may be characterized by any wavelength and/or power capable of initiating polymerization. Examples of wavelengths of light include ultraviolet (UV) or visible. UV light sources include UVA (wavelength about 400 nm to about 320 nm), UVB (about 320 nm to about 290 nm) or UVC (about 290 nm to about 100 nm). Any suitable source may be used, including laser sources. The source may be broadband or narrowband, or a combination. The light source may provide continuous or pulsed light during the process. Both the length of time the system is exposed to UV light and the intensity of the UV light can be varied to determine the ideal reaction conditions.

Examples of materials that may be printed on with the presently described methods and/or systems include, but are not limited to, those described in the following US Provisional Applications filed by Align Technology, Inc. on Jul. 7, 2015: "MULTI-MATERIAL ALIGNERS", U.S. Ser. No. 62/189,259; "DIRECT FABRICATION OF ALIGNERS WITH INTERPROXIMAL FORCE COUPLING", U.S. Ser. No. 62/189,263; "DIRECT FABRICATION OF ORTHODONTIC APPLIANCES WITH VARIABLE PROPERTIES", U.S. Ser. No. 62/189,291; "DIRECT FABRICATION OF ALIGNERS FOR ARCH EXPANSION", U.S. Ser. No. 62/189,271; "DIRECT FABRICATION OF ATTACHMENT TEMPLATES WITH ADHESIVE", U.S. Ser. No. 62/189,282; "DIRECT FABRICATION CROSSLINKING FOR PALATE EXPANSION AND OTHER APPLICATIONS", U.S. Ser. No. 62/189,301; "SYSTEMS, APPARATUSES AND METHODS FOR DENTAL APPLIANCES WITH INTEGRALLY FORMED FEATURES", U.S. Ser. No. 62/189,312; "DIRECT FABRICATION OF POWER ARMS", U.S. Ser. No. 62/189,317; "SYSTEMS, APPARATUSES AND METHODS FOR DRUG DELIVERY FROM DENTAL APPLIANCES WITH INTEGRALLY FORMED RESERVOIRS", U.S. Ser. No. 62/189,303 and "DENTAL APPLIANCE HAVING ORNAMENTAL DESIGN", U.S. Ser. No. 62/189,318, and any conversion applications thereof, and U.S. Pat. Pub. Nos. 20170007362 and 20170008333, each of the aforesaid are hereby incorporated by reference in its entirety.

Pretreatments of materials before printing may be accomplished by chemical treatments which react with the surface (oxidizers and other aggressive chemicals), plasticize or craze the surface (solvent like chemicals), and use of coupling agents (e.g. Silane chemistry and others). Mechanical pretreatment may involve roughing up the surface to create more surface area and more opportunities for mechanical bonding. Also, radiation treatments can be used to modify the surface such as x-ray or ultraviolet exposure. Other popular surface treatments that are used are plasma or corona treatments. Combinations of different types of pretreatments may also be used. The methods provided herein may also be used with a pretreatment to further increase the adhesion of the ink. Such pretreatment, however, is not as necessary and thus can be removed from the process to save a process step and equipment expense. It is understood that pretreatments are typically done on cleaned surfaces, and so if the surface has contaminations, there may be a washing or rinsing step whereby water, soap, $CO_2$ jet, alcohol, etc. may be used to clean the surface before pretreatment or as a part of pretreatment. When pretreatments are used in combination with the instantly described methods, corona and plasma pretreatments may be used.

In some embodiments, the low surface energy material to be printed onto can be any plastic. Some examples of plastics include polyolefins, polyesters, polyacrylates, polymethacrylates, polystyrenes, Polypropylenes, polyethylenes, Polyethylene terephthalates, poly lactic acid, polyurethanes, epoxide polymers, polyethers, poly(vinyl chlorides), polysiloxanes, polycarbonates, polyamides, poly acrylonitriles, polybutadienes, poly(cycloolefins), and copolymers. The systems and/or methods provided herein are compatible with a range of plastics. Accordingly, this list is not all inclusive, but rather is exemplary. The plastics can be thermosets or thermoplastics. The plastic may be a thermoplastic. The low surface energy material may be a polymer used as an aligner for orthodontic cases, including any of the removable orthodontic aligners described in any of U.S. Pat. Pub. Nos. 2017/0008333 and 2017/0007362 (Align Technology, Inc. San Jose, Calif.), which are specifically incorporated by reference for at least the aligners, materials formed into aligners, and methods of making such aligners.

A wide range of inks are compatible with the instantly described systems and/or methods. The inks can be any pigmented resin. In some embodiments, the inks are cured using heat, light (e.g., electromagnetic radiation), water, or air. Electromagnetic energy in the form of ultraviolet and visible light may be used. The inks typically contain dyes and/or pigments which can prevent a thick layer of ink from being cured by electromagnetic radiation, and in such cases dual cure systems (cationic and free radical) can be used or heated. In general, inks contain low molecular weight monomers (or solvents) which at temperatures well below the substrate's glass transition temperature ($T_g$) will not adequately penetrate into the polymer network of the substrate. However, if the polymer is near its $T_g$ or heated to be near its $T_g$, these low molecular weight compounds are able to diffuse into and plasticize the polymer. After these low molecular weight compounds are in the polymer, the curing process can begin whether by heat, light or other means. Once cured, the ink may be partially embedded into the substrate (interpenetrating network) and should have a large number of entanglements with the substrate polymer. Additionally, some polar bonding or even covalent bonding may occur. Such bonding may create effective adhesion between the ink and the substrate, including sufficient adherence for use in dental applications, including aligners, mouthguards, and the like.

Inks that use solvents are also compatible with the systems and/or methods described herein, and may function in a similar manner as other inks. In some embodiments, those inks and solvents, however, may need to contain low molecular weight monomers that are capable of penetrating into the substrate to later be cured. However, with both solvents and low molecular weight monomers, it is important to recognize that these compounds can evaporate from the surface. This is especially true as the substrate or the ink is heated. Accordingly, for each ink and each substrate, there is a matching of variables such as soak time, temperature, and evaporation rate being important.

In some embodiments, the amount of soak time may need to be adjusted to achieve desired outcomes. As an example, when conventional inks (e.g., those that are UV cured) are used, and when inkjet systems/processes are used to apply the ink to a substrate, the ink may be cured in a very short time (e.g., much less than a second) and at room temperature. When such an ink is in contact with a high glass transition temperature ($T_g$) material, the low molecular weight compounds do not have time to diffuse appreciably into the substrate. As the temperature of the substrate is increased, the rate of diffusion of the ink is increased (if there is some solubility). At temperatures below the polymer's $T_g$, soaking times need to be increased to allow the ink to penetrate into the substrate. As such, it has been found that having the substrate at 60° C. below its $T_g$ will require more than 10 seconds of soak time to obtain sufficient penetration of the ink to produce good adhesion. When less than 30° C. below the $T_g$, the soak times are decreased to 6 seconds. And when just 10° C. below the $T_g$, the soak time only needs to be 4 seconds. When at the $T_g$ or higher, the soak times can be less than 1 second and still achieve sufficient adhesion. These soak times are not considered absolute but are only to demonstrate the trend that is found between soak time and the $T_g$ of the material being printed onto. Different inks and different substrates will require different times, but the trend can be empirically determined to determine an ideal soak time. This can also be true for thermal curing, but in thermally cured systems, the soak time is typically sufficient. Therefore, for substrates with $T_g$'s higher than room temperature, they will greatly benefit from the instantly described methods for achieving adhesion.

Adhesion can be tested by any number of procedures, including to assess whether the ink adhesion is strong. Typical tests are by printing onto a substrate and then applying adhesive tape and removing the tape to see if the ink stays attached to the substrate or is pulled off with the tape. See ASTM D3359, ASTM D4541, or other ASTM testing protocols (available at www.astm.org). Adhesion may be tested after printing (and cooling to room temperature) and after the printed material has been immersed in water for 24 hours and dried. A more stringent adhesion test may include the crosshatch tape adhesion test where by a crosshatch is made into the cured ink and then tape is used as before to try and remove the ink. Any of the various testing methods for coating or ink adhesion can be used to measure the relative adhesion differences between the different methods of ink application. Depending on the application of interest, the adhesion requirement may be set at any desired level, up to and including minimal or no visible ink removed to the naked eye. For example, a tape test of adhesion may be characterized as meeting "durably adhered" when at least 90%, at least 95%, at least 99% or 100% of the ink initially adhered remains adhered to the material after a 24 hour water soak test for a specified temperature and liquid composition When applying the ink and using light to cure the ink, it can sometimes be advantageous to use an inert atmosphere to prevent oxygen inhibition at the surface of the ink. By light curing in an inert atmosphere (nitrogen, carbon dioxide, or others), the surface of the ink can be cured tack free. When oxygen is present, a stronger light source and a larger amount of photoinitiator is required in the ink formulation to cure the ink to a tack free surface finish. Also, thiols and other additives can be used to reduce the effects of oxygen inhibition. The photoinitiator in the formulation is typically greater than 1 wt % of the formulation and sometimes greater than 5 wt % depending on the dye or pigment used. Typical concentrations may be between 1 wt % to 6 wt %, and any subranges thereof. When inert atmospheres, thiols, and/or other additives for reducing the effects of oxygen inhibition are used, the amount of photoinitiator can be less than 1 wt %. Accordingly, typical concentrations in such processes may be between 0.1 wt % and 1 wt %, and any subranges thereof. The methods provided herein preferably have less photoinitiator in the formulations, particularly because the photoinitiators are typically leachable components. To avoid unwanted leaching impacts, an oligomeric, polymeric, or reactive group functionalized photoinitiator may be used.

In the application of the ink, viscosities of less than 100 cps are typically used for inkjet methods. While solvents are often used to achieve this and lower viscosities, it is preferred to use ink formulations with no solvents. Also, it can be beneficial to heat the ink before it is jetted so that it is of a lower viscosity than if it were not heated. This allows one to use higher molecular weight monomers and also can assist in diffusion into the substrate if the ink is still hot when it contacts the surface. Ink temperatures of greater than 60° C. show some adhesion benefit, while ink temperatures greater than 100° C. are preferred. A combination of heated ink and heated substrate provides improved adhesion characteristics.

Heating of the substrate can be accomplished by a wide range of techniques, including but not limited to radiative heating or convective heating. Radiative heating may be accomplished using infrared light. Efficient infrared heating may be by matching the infrared source to the absorption bands of the substrate so that the substrate efficiently absorbs the energy. By doing this, only the surface of the substrate is heated (which is advantageous for preventing changes to the bulk material). It is sometimes advantageous to heat only the area to be printed to. In such an embodiment, the area that is to be printed onto is heated with any of several methods that allow for local heating of the substrate while allowing the rest of the substrate surface, where printing will not occur, to remain cool. This can be helpful when the heating the substrate can lead to changes in the substrate shape, crystallinity, or other properties. To achieve local heating to an area to be printed, an IR light source or hot air jet may need to be directed at the area to be printed. An infrared thermal sensor can be used to measure the temperature during and after the heating step. Once the desired temperature is in the desired range, printing can occur. Thus, any of the methods provided herein may use heating of only a portion of the substrate, and further, heating only the surface of the substrate to be printed onto. This aspect may be quantified and described in terms of a total heated surface area that substantially corresponds to the printed area, such as a printed area that occupies at least 10%, at least 30%, at least 50% or at least 75% of the heated area. For example, where an alphanumeric label is to be printed onto the surface, a rectangular shape may be heated on the surface and the alphanumeric label (or any other design) is printed within the rectangular shape. Similarly, any other geometric shapes may be heated onto the surface, such as a square, triangle, circle, ellipse or polygon. Heating by IR may be used with appropriate focusing lenses and filters to achieve the desired heating shape on the surface.

The methods are further compatible with processes where the ink is applied to the surface and then the surface heated. When this approach is used, it is possible to use the ink as a heat source by using infrared wavelengths that only the ink appreciably absorbs. In this manner, only the surface that the ink is contacting is heated to facilitate the diffusion of the ink into the substrate.

Other energy forms may be used to heat the substrate or ink such as microwave radiation, contact heating with a hot element, ultrasonic waves, radio frequency heating, hot air or liquid, and/or others. Any one or more components may be used to provide controlled heating of the substrate or ink, including dispersive components, lenses, filters, masks or the like. The heating source may in some embodiments be residual heat from a thermoforming process. While the material is still a part of the mold, the material temperature may be greater than the $T_g$ of the material during the ink jetting process as the mold may minimize risk of unwanted material deformation.

Any of the methods may be used with a coating application to the printed area after the ink is cured. Such overcoats or protective coats serve to further protect the printing against abrasion and wearing and/or decrease the amount of leaching of materials from the ink out of the cured ink.

Figure 1B:
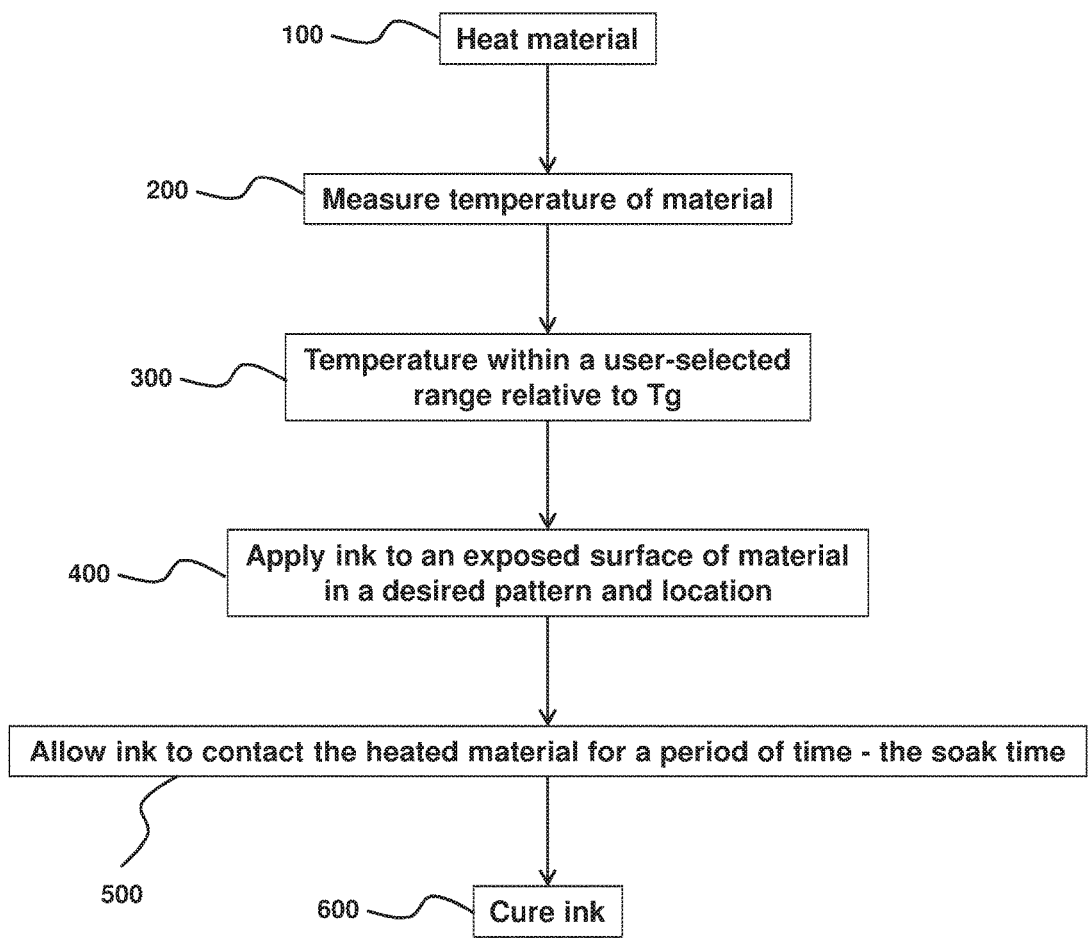

FIGS. 1A and 1B are flow-chart summaries of examples of methods of ink-jet printing to a surface of a material.

Turning to FIG. 1A, a material may be obtained. The material may include a low surface energy material. The material obtained may be generally characterized as hydrophobic or non-polar, and so does not receive printable ink well, and provides challenges for achieving good ink adhesion to a surface. As noted herein, the material may comprise one or more plastics, including but not limited to: polyolefins, polyesters, polyacrylates, polymethacrylates, polystyrenes, Polypropylenes, polyethylenes, Polyethylene terephthalates, poly lactic acid, polyurethanes, epoxide polymers, polyethers, poly(vinyl chlorides), polysiloxanes, polycarbonates, polyamides, poly acrylonitriles, polybutadienes, poly(cycloolefins), and copolymers. The materials can be thermoset or thermoplastics. The material may be a polymer used as an aligner for orthodontic cases, including any of the removable orthodontic aligners described in any of U.S. Pat. Pub. Nos. 2017/0008333 and 2017/0007362.

At an operation 100, the material is heated. In some embodiments, the material may be heated to a temperature less than the glass transition temperature ($T_g$) of the material. In some embodiments, the elevated temperature may comprise a value to facilitate ink penetration. Relevant heating techniques include radiative heating, convective heating, etc. As discussed herein, the heating may be of a surface only, or a subregion of the surface that generally corresponds to the printing region. As also discussed herein, in some embodiments, heated ink may be applied to the material to facilitate penetration into the material and/or heat the material.

At an operation 200 (see FIG. 1B), the temperature of the material may be measured. Measurement of temperature of the material may form the basis of confirmation that the low surface energy material is at the temperature less than the glass transition temperature.

At an operation 300 (see FIG. 1B), it is determined whether, after heating, the temperature of the material falls within a user-selected range relative to the glass transition temperature ($T_g$) of the material. A "user-selected range," as used herein, may include a range of temperatures selected by a user and below the glass temperature ($T_g$) of the material. In some embodiments, the "user-selected range" of the temperature may fall within an elevated temperature to facilitate ink penetration that is below the glass temperature ($T_g$) of the material.

At an operation 400 (see FIGS. 1A and 1B) ink may be applied to an exposed surface of the material in a desired pattern and location. In some embodiments, the operation 400 is performed if at least the printing area has the desired temperature as indicated by the operation 300. As noted herein, in some embodiments, the ink itself may have been heated so to cause at least a part of the material to become heated to an elevated temperature below the glass temperature ($T_g$) of the material.

At an operation 500 (see FIGS. 1A and 1B), the applied ink is allowed to contact and/or adhere to the heated material for a specified amount of time. In some embodiments, the specified amount of time corresponds to a "soak time," to ensure the ink sufficiently penetrates the material so to be durably adhered to the material after a curing operation, 600, in which the ink, the material, and/or the combination thereof is cured using the techniques described herein.

Figure 2:
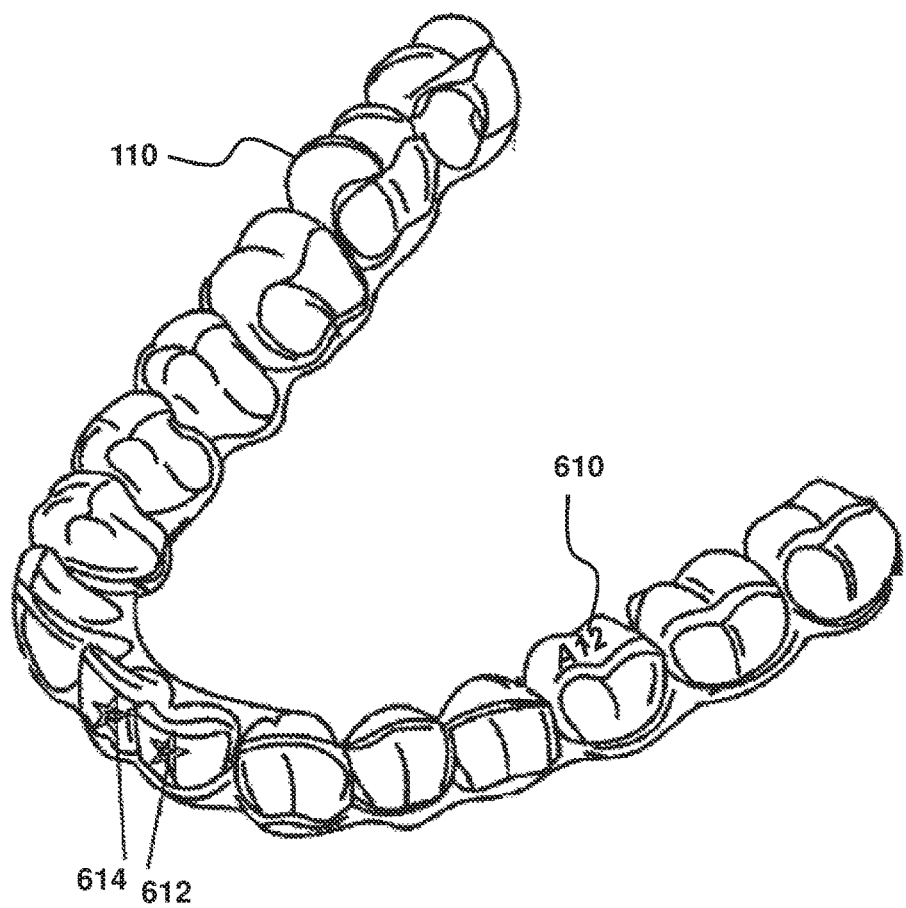
FIG. 2 is a schematic illustration of a resultant product that uses an example of an instantly described method to obtain various designs and information on exposed surfaces of a dental aligner.

FIG. 2 is a schematic illustration of a resultant product that uses an example of the methods described herein to obtain various designs and information on exposed surfaces of a dental aligner. In some embodiments, FIG. 2 illustrates a resultant device, in this case an aligner 110, after the printing method. Any number of printed regions and corresponding printed patterns may be provided, as indicated by alphanumeric characters 610 (A12) on a top surface and star logo 612 and 614 on the front surface of the aligner. In some embodiments, the printed patterns may include any pattern, alphanumeric sequence, graphical depiction, etc. Accordingly, provided herein are aligners with one or more printed regions provided by any of the methods described herein.

Figure 3:
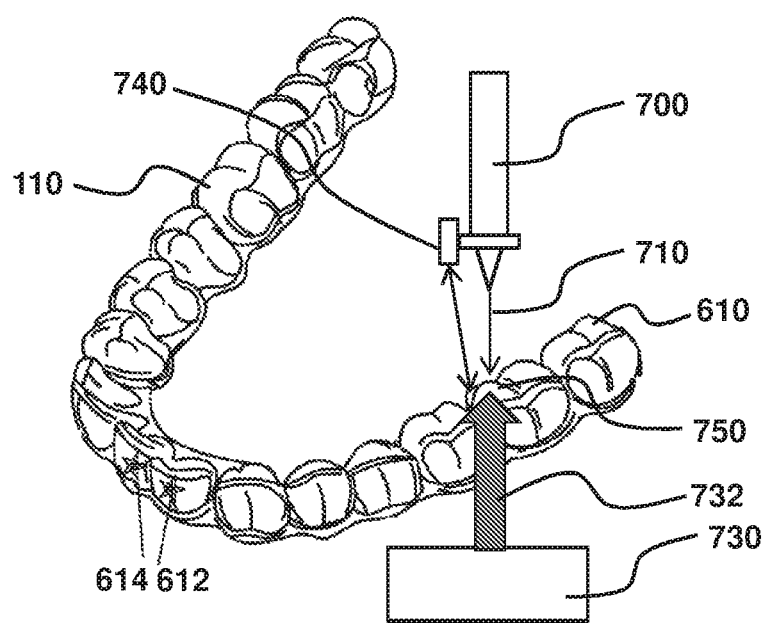
FIG. 3 is a schematic illustration of an example of an inkjet printer applying printable ink to a low surface energy material that is a dental aligner.

FIG. 3 is a schematic illustration of an example of an ink-jet printer applying printable ink to a low surface energy material that is a dental aligner. In the example of FIG. 3, there is shown a system for printing ink 710 onto an exposed surface 610 of a low energy material 110, illustrated as a dental aligner. In this example, an ink-jet printer 700 is positioned in fluid communication with the low surface energy material, such as to facilitate application of ink onto the exposed surface, indicated by arrow 710. This can be achieved by a substrate support (not shown) that holds the material at a desired position. The substrate support may provide controlled movement of material 110, so that different surfaces may be printed, as illustrated by printed designs 612 and 614. Alternatively or in addition, the nozzle of ink jet printer 700 may be movable. Heater 730 may provide controlled heating to a printable area 750. The heating may be localized, as represented by arrow 732. Temperature sensor 740 may measure temperature in or adjacent to printable area 750, so that the ink application 710 by ink jet printer 710 occurs at a desired elevated temperature. The ink-jet printer may be operably connected to a fabrication platform (not shown) for making a device from said low surface energy material. For example, the material may form a dental aligner and the fabrication platform comprise a 3-D printer or a mold system in which a pre-polymer is polymerized in a desired three-dimensional shape.

Example: An aligner was thermoformed then an infared light source was used to warm the aligner surface to 80° C. An injet device was then used to apply ink to the surface of the Aligner. The ink was allowed to soak for varying times. For the particular formulation of ink used, the adhesion reached a maximum in performance of 100% retention of the printed image (as measured by a 24 hour soak and cross hatch adhesion test) after 3 seconds of soak time. After greater than 10 seconds soak time at that 80° C., the adhesion starts to decrease. It is believed that the lower molecular components of the ink are evaporating and thus changing the cured properties of the ink in a detrimental way for durable adhesion. Ink jetted samples with a 4 sec soak time are sent for cytotox testing and passed; thus the cured ink was considered not toxic to living cells.

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

It must be noted that as used herein and in the appended claims, the singular forms "a", "an", and "the" include plural reference unless the context clearly dictates otherwise. Thus, for example, reference to "a component" includes a plurality of such components and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method comprising:
   obtaining an orthodontic appliance having a material characterized by a glass transition temperature;
   bringing the material of the orthodontic appliance to a specified temperature;
   applying a formulation to a region of the material while the material is within a range of the specified temperature;
   maintaining the applied formulation and the region of the material at the specified temperature for a soak time; and
   curing the applied formulation to the material using electromagnetic radiation after the soak time to obtain a printed orthodontic device.

2. The method of claim 1, wherein applying the formulation to the region of the material comprises forming on the material a design, information, or some combination thereof.

3. The method of claim 1, wherein applying the formulation to the region of the material comprises printing the formulation onto the region.

4. The method of claim 1, further comprising treating a surface of the material before bringing the material to the specified temperature.

5. The method of claim 1, further comprising treating a surface of the material before bringing the material to the specified temperature, wherein treating the surface comprises performing a chemical treatment to the surface, performing a mechanical treatment to the surface, performing a radiation treatment to the surface, performing a plasma treatment to the surface, performing a coronal treatment to the surface, or some combination thereof.

6. The method of claim 1, wherein the material comprises one or more of: polyolefin, polyester, polyacrylate, polymethacrylate, polystyrene, polypropylene, polyethylene, polyethylene terephthalate, poly lactic acid, polyurethane, epoxide polymer, polyether, poly(vinyl chloride), polysiloxane, polycarbonate, polyamide, poly acrylonitrile, polybutadiene, poly(cycloolefin), and co-polymer.

7. The method of claim 1, wherein the formulation contains a curable ink.

8. The method of claim 1, wherein the formulation comprises a curable resin.

9. The method of claim 1, wherein the formulation contains a substance comprising a dye, a pigment, or a combination thereof, and the substance can prevent at least a part of the applied formulation from being cured by the electromagnetic radiation.

10. The method of claim 1, wherein the formulation contains a compound that has limited penetration to a depth of a polymer network of the material when at temperatures below the glass transition temperature of the material.

11. The method of claim 1, wherein the formulation contains a compound that has limited penetration to a depth of a polymer network of the material when at temperatures below the glass transition temperature of the material, and wherein the compound comprises a monomer, a solvent, or a combination thereof.

12. The method of claim 1, wherein the formulation contains a compound that penetrates to a depth of a polymer network of the material when at temperatures near the glass transition temperature of the material.

13. The method of claim 1, wherein the formulation contains a compound that penetrates to a depth of a polymer network of the material when at temperatures near the glass transition temperature of the material, and the compound comprises a monomer, a solvent, or a combination thereof.

14. The method of claim 1, wherein the soak time is a function of a difference between the specified temperature and the glass transition temperature of the material.

15. The method of claim 1, wherein the specified temperature is within 70° C. of the glass transition temperature of the material.

16. The method of claim 1, wherein the specified temperature is within 20° C. of the glass transition temperature of the material.

17. The method of claim 1, further comprising testing adhesion of the applied formulation to the material with adhesive tape.

18. The method of claim 1, wherein curing the applied formulation to the material is performed in an inert atmosphere to prevent oxygen inhibition at a surface of the applied formulation.

19. The method of claim 1, wherein bringing the material of the orthodontic appliance to the specified temperature comprises heating the material.

20. The method of claim 1, wherein bringing the material of the orthodontic appliance to the specified temperature comprises directing a light source or a hot air jet at the material.

21. The method of claim 1, further comprising adding a coating to the material after curing the applied formulation to the material.

22. The method of claim 1, wherein the material is a polymer.

23. A method comprising:
   obtaining an orthodontic appliance having a material characterized by a glass transition temperature, the material comprising one or more of: polyolefin, polyester, polyacrylate, polymethacrylate, polystyrene, polypropylene, polyethylene, polyethylene terephthalate, poly lactic acid, polyurethane, epoxide polymer, polyether, poly(vinyl chloride), polysiloxane, polycarbonate, polyamide, poly acrylonitrile, polybutadiene, poly(cycloolefin), and co-polymer;

bringing the material of the orthodontic appliance to a specified temperature within 20° C. of the glass transition temperature of the material;

printing, with an inkjet printer, a formulation to a region of the material while the material is within a range of the specified temperature;

maintaining the printed formulation and the region of the material at the specified temperature for a soak time, the soak time being a function of a difference between the specified temperature and the glass transition temperature of the material; and curing the printed formulation to the material using electromagnetic radiation after the soak time to obtain a printed orthodontic device.

24. A printed orthodontic appliance formed by a method comprising:

obtaining an orthodontic appliance having a material characterized by a glass transition temperature;

bringing the material of the orthodontic appliance to a specified temperature;

applying a formulation to a region of the material while the material is within a range of the specified temperature;

maintaining the applied formulation and the region of the material at the specified temperature for a soak time; and curing the applied formulation to the material using electromagnetic radiation after the soak time to obtain the printed orthodontic appliance.

* * * * *